(12) United States Patent
Cooney, III et al.

(10) Patent No.: US 6,302,915 B1
(45) Date of Patent: Oct. 16, 2001

(54) ULNAR IMPLANT SYSTEM

(75) Inventors: William P. Cooney, III; Richard A. Berger; Ronald L. Linscheid, all of Rochester; David A. Leibel, Princeton, all of MN (US)

(73) Assignee: The Mayo Foundation for Medical Education & Research, Rochester, MN (US)

( * ) Notice: Subject to any disclaimer, the term of this patent is extended or adjusted under 35 U.S.C. 154(b) by 0 days.

(21) Appl. No.: 09/650,541

(22) Filed: Aug. 30, 2000

(51) Int. Cl.$^7$ ........................................... A61F 2/42
(52) U.S. Cl. .................. 623/21.12; 623/21.11; 623/18.11
(58) Field of Search ............... 623/21.11, 21.12, 623/21.13, 21.15, 20.11, 18.11

(56) References Cited

U.S. PATENT DOCUMENTS

| | | |
|---|---|---|
| 3,593,342 | 7/1971 | Neibauer . |
| 3,875,594 | 4/1975 | Swanson . |
| 4,178,640 | 12/1979 | Buechler . |
| 4,180,871 * | 1/1980 | Hamas ........................... 623/21.11 |
| 4,229,841 | 10/1980 | Youm . |
| 4,242,759 | 1/1981 | White . |
| 4,944,758 | 7/1990 | Bekki . |
| 5,037,440 | 8/1991 | Koenig . |
| 5,108,444 * | 4/1992 | Branemark ..................... 623/21.12 |
| 5,133,762 | 7/1992 | Branemark . |
| 5,522,900 | 6/1996 | Hollister . |
| 5,782,926 | 7/1998 | Lamprecht . |
| 5,951,604 * | 9/1999 | Scheker ......................... 623/21.12 |

* cited by examiner

*Primary Examiner*—Pedro Philogene
(74) *Attorney, Agent, or Firm*—Nydegger & Associates

(57) ABSTRACT

An anatomical prosthesis for implantation after a resection of the distal ulna includes a head and a stem. The head is formed with a curved surface for articulation with the sigmoid notch of the distal radius. A bore is provided in the head to allow for attachment of the head to the stem. The head is further formed with suture holes for anchoring the head to the soft tissues such as the ulnar collateral capsule, the triangular fibrocartilage and the extensor carpi ulnaris subsheath that are exposed after resection of the distal ulna. The stem is elongated, having a proximal end for engagement with the intramedullary canal of the ulna, and a distal end for engagement with the bore formed in the head.

20 Claims, 3 Drawing Sheets

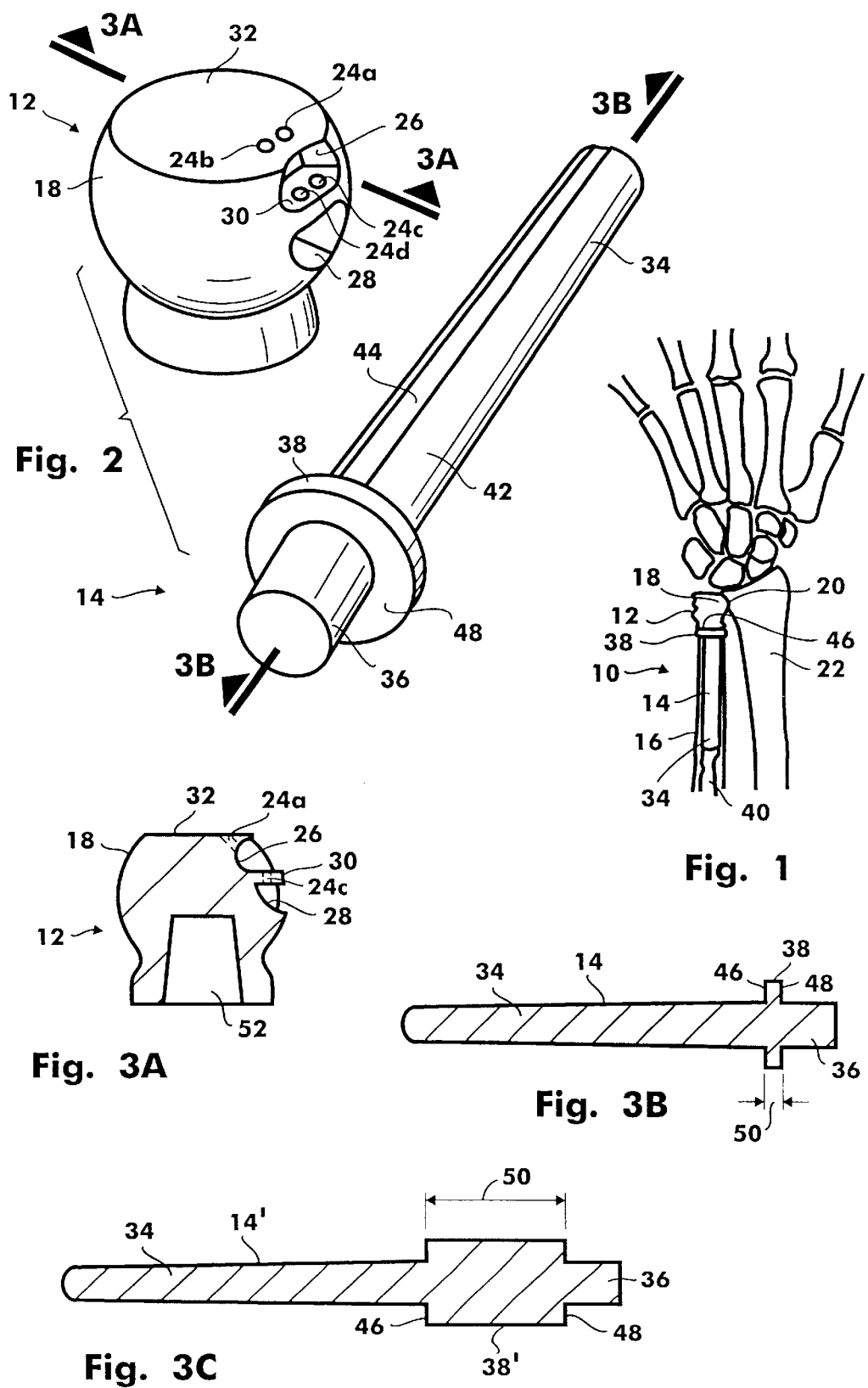

ULNAR IMPLANT SYSTEM

FIELD OF THE INVENTION

The present invention pertains generally to prostheses. More particularly, the present invention pertains to a prosthesis for the distal ulna. The present invention is particularly, but not exclusively, useful as an anatomic distal ulnar prosthesis.

BACKGROUND OF THE INVENTION

The distal radioulnar joint is a "shallow socket" ball joint. The radius articulates in pronation and supination on the distal ulna. The ulna, a relatively straight forearm bone linked to the wrist, translates dorsal-palmarly to accept the modestly bowed radius. Since the sigmoid fossa socket in most wrists is relatively flat, ligaments are required to support the distal ulna. These ligaments include the triangular fibrocartilage (TFC), the extensor carpi ulnaris (ECU) subsheath, and the ulnar collateral ligament complex. The stabilizing elements of the triangular fibrocartilage (TFC), extensor carpi ulnaris (ECU) subsheath, and the ulnar collateral complex are well recognized along with the importance of a distal ulna component (ulnar head) for transfer of compressive loads between the ulnar carpus and the distal ulna across the distal radioulnar joint.

Ligament disruption, ulnar styloid fractures, and fractures into the distal radioulnar joint are common occurrences following fractures of the distal radius and other rotational instability injuries of the forearm. Fracture or dislocation involving the distal radioulnar joint often results in a loss of forearm rotation related to either instability or incongruity between the sigmoid fossa of the distal radius and the ulnar head. A variety of different fractures involving the distal radius can cause this condition including the Colles' fracture and the Galeazzi fractures.

When there is loss of stability of the distal radioulnar joint, there is subsequent weakness in grip and pinch as well as potential loss of forearm rotation. Instability can also be associated with either an injury to the triangular fibrocartilage or to the ulnar styloid. When instability is present, a number of ligament reconstructive procedures have been devised to assist in treating the unstable distal ulna. Unfortunately, ligament reconstruction of the distal ulna is often incomplete in restoring stability, and joint replacement is often necessary.

Where there is an incongruity of the joint surface involving either the articulation of the ulnar head with the sigmoid fossa of the distal radius, or if there is a significant ulnar impaction syndrome between the distal articular surface of the head of the ulna and the ulna carpus, a joint replacement may be necessary. Specifically, this can include either joint replacement of the distal ulna or operative procedures designed to shorten the ulna or resect all or part of the distal ulna (i.e. Darrach, Bowers, or matched resection procedures). Unfortunately, there have been variable results associated with the partial or complete resections of the distal ulna, particularly those performed by open resection. For example, when the ulna is resected, and not replaced with a prosthesis, both instability of the wrist and "snapping" of the forearm in rotational pronation/supination can occur.

The primary indications, therefore, for reconstruction of the distal radioulnar joint by prosthetic replacement (ulnar head replacement only) are generally related to a fracture of the distal ulna or a fracture extending into the distal radioulnar joint producing post-traumatic arthritis. Degenerative arthritis from other causes is also a primary indication. This is considered if there is associated arthritis and an ulnar shortening procedure is contraindicated. A third condition for primary ulna replacement is rheumatoid arthritis with a painful and unstable distal radioulnar joint. In these situations, prosthetic replacement of the distal ulna with soft tissue advancement can be beneficial.

A distal ulnar prosthesis is also suitable to correct a previous resection of the distal ulna that has failed. Such will be the case for 1) partial resection of the joint articular surface, as described by Feldon, Bowers, or Watson, or 2) complete resection of the distal ulna as recommended by Darrach, Baldwin, and others. When faced with failed distal ulna resection, one has options towards reconstruction without restoring the distal radioulnar joint (DRUJ). For example, a failed distal ulna can be corrected by a pronator quadratus interposition, or, if there has been only a partial resection, a fusion of the distal radioulnar joint combined with a proximal pseudarthrosis (Suave-Kapandji procedure). These procedures, however, do not restore the normal DRUJ function of motion or load transfer and may be associated with instability of the distal ulna and proximal impingement of the ulna on the distal radius. In these cases, a distal ulna prosthesis is generally preferable. A distal ulnar prosthesis is also suitable to correct a previous prosthetic replacement such as a silicone ulnar head replacement which has failed.

Unfortunately, attempts to create a suitable distal ulnar prosthesis that provides adequate stabilization and support have heretofore failed. Although biomechanics research studies have clearly demonstrated a need for prosthetic replacement of the distal ulna for load sharing across the carpus (Palmer et al, Berger), an adequate prosthesis for the distal ulna has heretofore been unavailable.

In light of the above it is an object of the present invention to provide a distal ulnar prosthesis which is attachable to a soft tissue pocket that includes the triangular fibrocartilage, ECU subsheath, and ulnar collateral ligament complex to thereby maintain distal radioulnar joint stability. It is another object of the present invention to provide a distal ulnar prosthesis which aligns anatomically with the sigmoid fossa of the distal radius and is isosymmetric with the anatomic center of rotation of the forearm. It is yet another object of the present invention to provide an anatomic distal ulnar prosthesis that duplicates the normal articulation of the distal ulna with the radius. It is yet another object of the present invention to provide a distal ulnar prosthesis that allows for a normal forearm rotation of approximately 150–170°. Yet another object of the present invention is to provide a distal ulnar prosthesis which is relatively easy to implant, relatively simple to manufacture, and comparatively cost effective.

SUMMARY OF THE PREFERRED EMBODIMENTS

The present invention is directed to an anatomical prosthesis for implantation after a resection of the distal ulna. The prosthesis includes a head and a stem to replace the distal ulna. For the present invention, the head is formed with a curved surface for articulation with the sigmoid notch of the distal radius. As discussed below, a bore is provided in the head to allow attachment of the head to the stem. The head is further formed with suture holes for anchoring the head to the soft tissues that are exposed after resection of the distal ulna. These soft tissues include the ulnar collateral capsule, the triangular fibrocartilage and the extensor carpi ulnaris subsheath.

In the preferred embodiment of the present invention, the stem is elongated, having a proximal end for engagement with the intramedullary canal of the ulna, and a distal end for engagement with the bore formed in the head. The elongated stem is formed with a collar located between the proximal end of the stem and the distal end of the stem. The collar is formed with a substantially flat proximal surface and a substantially flat distal surface. The proximal surface of the collar provides a buttress for the stem, preventing excessive penetration of the stem into the intramedullary canal of the ulna. Preferably, the collar is approximately two millimeters (2 mm) in length (measured as the distance between the distal surface of the collar and the proximal surface of the collar). A prosthesis in accordance with the present invention having a longer collar length, such as a collar length of approximately twenty to thirty millimeters (20–30 mm) can be used in a patient who has undergone a Darrach resection or other procedure that involves excision of all or part of the distal ulna.

For the present invention, the proximal end of the stem projects from the proximal surface of the collar. Further, the proximal end of the stem is tapered with a proximally decreasing cross-section to facilitate the insertion of the proximal end of the stem into the intramedullary canal of the ulna. Preferably, the surface of the proximal end of the stem can be formed with a roughened texture to allow for a cement-free joint between the stem and the ulna. Additionally, the surface of the proximal end of the stem can be coated. Examples of coatings that may be used alone or in combination include titanium, hydroxyapatite and a sintered bead coating such as cobalt chromium. Optionally, flutes can be formed in the proximal end of the stem to prevent rotation of the stem in the intramedullary canal of the ulna.

Also for the present invention, the distal end of the stem projects from the distal surface of the collar. Further, the distal end of the stem is tapered with a distally decreasing cross-section. Similarly, the bore formed in the head is tapered with a distally decreasing cross-section. Preferably, both tapers are Morse tapers. The tapers are provided to secure the stem to the head when the distal end of the stem is engaged with the bore of the head.

To implant the distal ulnar prosthesis in the patient, the distal ulna is first exposed and resected. Preferably, the distal ulna is exposed by making an incision along the medial shaft of the distal ulna in line with the ulnar styloid. A prior dorsal incision can also be utilized to expose the distal ulna. Next, a template can be located distally over the articular surface of the distal ulna to mark the prescribed resection length. Once the resection length is marked, an oscillating saw can be used to resect the distal ulna, exposing the intramedullary canal and the soft tissues that formerly surrounded the distal ulna. These soft tissues include the ulnar collateral capsule, the triangular fibrocartilage and the extensor carpi ulnaris subsheath. Once exposed, the intramedullary canal can be identified with an awl or sharp broach and then reamed to the appropriate stem size.

Prior to implantation of the prosthesis, a trial stem and head can be inserted and tested to verify anatomical alignment and to ensure that the proper resection length has been achieved. After removal of the trial stem and head, the stem of the prosthesis can be inserted into the intramedullary canal of the ulna to anchor the prosthesis to the ulna. Specifically, the proximal end of the stem can be advanced into the intramedullary canal using an impactor until the proximal surface of the collar contacts and seats on the ulna. If a firm fit is not obtained between the stem and the ulna after impaction of the stem, a bone cement such as polymethylmethacrylate can be used to cement the stem to the ulna. The fit between the stem and the distal ulna can be assessed by applying a distal traction on the stem of the prosthesis. Any movement of the stem in the intramedullary canal of the distal ulna indicates that a firm fit has not been obtained.

After the proximal end of the stem has been secured to the ulna, the head can be sutured to the soft tissue formerly surrounding the distal ulna using the suture holes formed in the head. For this purpose, non-absorbable sutures can be used. A minimum of five knotted suture passes with a 2.0 suture is preferred. Once the ulnar collateral capsule, the triangular fibrocartilage and the extensor carpi ulnaris subsheath are sutured to the head, the head can be impacted onto the stem. Specifically, the distal end of the stem can be inserted in the bore formed in the head. Next, the head can be advanced onto the stem with an impactor until a secure fit is obtained between the head and the stem. After the head is attached to the stem, the sutures can be tied into the capsular sleeve surrounding the distal ulnar prosthesis and the subcutaneous tissues and skin can be closed over the prosthesis.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a skeletal view of the human forearm after implantation of a distal ulnar prosthesis in accordance with the present invention;

FIG. 2 is a perspective view of a prosthesis in accordance with the present invention showing the head and stem;

FIG. 3A is a cross sectional view of a head as seen along line 3A—3A in FIG. 2;

FIG. 3B is a cross sectional view of a stem as seen along line 3B—3B in FIG. 2;

FIG. 3C is a cross sectional view as in FIG. 3A showing a stem with an extended collar for implantation in a patient who has undergone a Darrach or other similar resection;

DESCRIPTION OF THE PREFERRED EMBODIMENT

Figure 4:
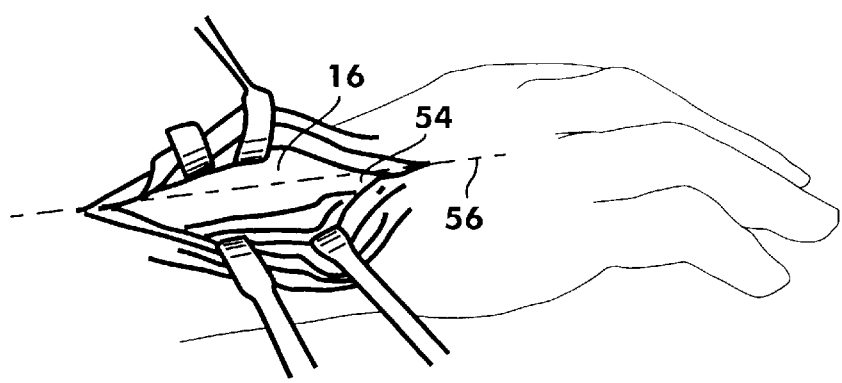
FIG. 4 is a perspective view of a forearm after a surgical incision has been performed to expose the distal ulna.
Figure 5:
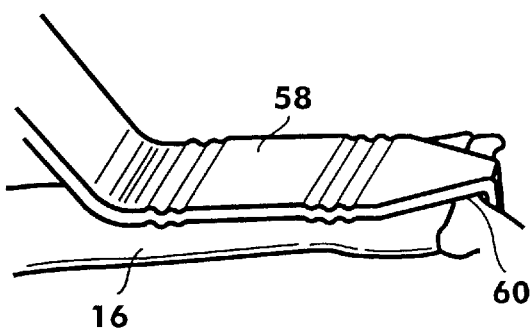
FIG. 5 is a perspective view of the distal ulna showing a template positioned for marking the appropriate resection length.

Referring to FIG. 1, a prosthesis for the distal ulna in accordance with the present invention is shown and generally designated 10. As shown in FIG. 1, the prosthesis 10 includes a head 12 attached to a stem 14. For the present invention, the prosthesis 10 is intended to be an anatomical replacement for the distal ulna 16 after its resection. By cross-referencing FIGS. 1, 2 and 3A is can be seen that the head 12 is generally crown shaped and formed with a curved surface 18 for articulation with the sigmoid notch 20 of the distal radius 22. In the preferred embodiment of the present invention, the head 12 is made of a cobalt chrome material, and the surface 18 is highly polished, allowing for smooth articulation between the surface 18 and the sigmoid notch 20 of the radius 22. Importantly, the head 12 is formed with suture holes 24a–d for anchoring the head 12 to the soft tissues exposed after resection of the distal ulna 16. As shown in FIGS. 2 and 3A, indentations 26, 28 can be formed in the head 12 to accommodate the suture holes 24. In the preferred embodiment of the present invention, a ledge 30 is formed between indentation 26 and indentation 28. As shown, suture hole 24c and suture hole 24d extend through the ledge 30, from indentation 26 to indentation 28. Further, as shown, suture hole 24a and suture hole 24b extend from the top surface 32 of the head 12 to the indentation 26. Although four suture holes 24a–d are shown in the preferred embodiment for the present invention, it is to be appreciated any number of suture holes 24 can be used in accordance with the present invention. Further, although two indentations 26, 28 and a ledge 30 are used as a platform in the head 12 for suture holes 24c,d, other designs to create suture holes 24 can be used.

With combined reference to FIGS. 1, 2 and 3B, it can be seen that the stem 14 is elongated and formed with a proximal end 34 and a distal end 36. In the preferred embodiment of the present invention, a collar 38 is formed on the stem 14 between the distal end 36 and the proximal end 34. Preferably, the stem 14 is made of cobalt chrome or titanium. As shown in FIG. 1, the proximal end 34 is shaped for insertion into the intramedullary canal 40 of the distal ulna 16, to thereby anchor the prosthesis 10 to the distal ulna 16. For the present invention, the proximal end 34 of the stem 14 is preferably tapered with a proximally decreasing cross-section to facilitate the insertion of the proximal end 34 of the stem 14 into the intramedullary canal 40 of the distal ulna 16. Further, the surface 42 of the proximal end 34 can be formed with a roughened texture, as shown in FIG. 2, to allow for a cement-free joint between the stem 14 and the distal ulna 16. Additionally, or in lieu of texturing, the surface 42 can be coated (not shown) with a coating such as titanium, hydroxyapatite or a sintered bead coating such as cobalt chromium. Optional flutes 44 can be formed in the proximal end 34 of the stem 14 to prevent rotation of the stem 14 in the intramedullary canal 40 of the distal ulna 16.

Referring now to FIG. 3B, the collar 38 is formed with a substantially flat proximal surface 46 and a substantially flat distal surface 48. The proximal surface 46 of the collar 38 provides a buttress for the stem 14 preventing excessive penetration of the stem 14 into the intramedullary canal 40 of the distal ulna 16. Preferably, the length 50 measured as the distance between the distal surface 48 and the proximal surface 46 of the collar 38 is approximately two millimeters (2 mm). As shown in FIG. 3C, a stem 14' in accordance with the present invention having an extended collar 38' can be provided for use in a patient who has undergone a Darrach resection. Specifically, the extended collar 38' for use after a Darrach or other similar resection preferably has a length 50 of between approximately twenty millimeters and approximately thirty millimeters (20–30 mm).

The cooperation of structure between the head 12 and the stem 14 can best be understood with reference to FIGS. 3A and 3B. As shown in FIG. 3A, the head 12 is formed with a bore 52 that is tapered with a distally decreasing cross-section. Also, as shown in FIG. 3B, the distal end 36 of the stem 14 projects from the distal surface 48 of the collar 38 and is tapered with a distally decreasing cross-section. The distal end 36 of the stem 14 is sized and tapered to provide a secure fit between the head 12 and the stem 14 when the distal end 36 of the stem 14 is inserted in the bore 52 of the head 12. Preferably, both the taper of the bore 52 and the taper of the distal end 36 are Morse tapers. Although a two-piece prosthesis 10 having a separate head 12 that is engageable with a separate stem 14 is shown and described above, it is to be appreciated that the head 12 and stem 14 may be formed as a one-piece prosthesis 10.

Figure 6:
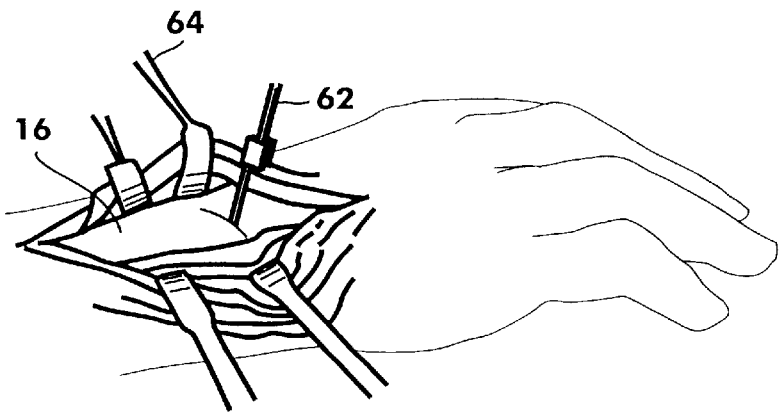
FIG. 6 is a perspective view of a forearm showing the resection of the distal ulna using an oscillating saw.

FIGS. 4–9 show, in overview, a procedure for implantation of a prosthesis 10 in accordance with the present invention. As shown in FIG. 4, the distal ulna 16 is first exposed. Preferably, the distal ulna 16 is exposed by making an incision along the medial shaft of the distal ulna in line with the ulnar styloid 54 (i.e. an incision along line 56 shown in FIG. 4). Alternatively, a dorsal incision (not shown) centered over the distal radioulnar joint in line with the fourth metacarpel can be used to expose the distal ulna 16. Once exposed, a template 58 can be placed against the distal ulna 16 and located distally over the articular surface 60 of the distal ulna 16 to mark the prescribed resection length. The resection length can be marked on the distal ulna 16 with a pen or osteotome (not shown). Referring now to FIG. 6, after marking the resection length, an oscillating saw 62 can be used to resect the distal ulna 16, exposing the intramedullary canal 40 (shown in FIG. 1) and the soft tissues that formerly surrounded the distal ulna 16. As further shown in FIG. 6, Hohmann retractors 64 can be used to slightly elevate the distal ulna 16 during resection. Once exposed, the intramedullary canal 40 can be identified with an awl or sharp broach (not shown) and then reamed to accommodate the appropriately sized stem 14.

Prior to implantation of the prosthesis 10, a trial stem and trial head (not shown) can be inserted and tested to verify anatomical alignment and to ensure that the proper resection length has been achieved. Referring now to FIG. 1, after removal of the trial stem and trial head, the stem 14 of the prosthesis 10 can be inserted into the intramedullary canal 40 of the distal ulna 16 to anchor the prosthesis 10 to the distal ulna 16. Specifically, the proximal end 34 of the stem 14 can be advanced into the intramedullary canal 40 using an impactor (not shown) until the proximal surface 46 of the collar 38 contacts and seats on the distal ulna 16. If a firm fit is not obtained between the stem 14 and the distal ulna 16 after impaction of the stem 14, a bone cement (not shown) such as polymethylmethacrylate can be used to cement the stem 14 to the distal ulna 16.

Figure 7:
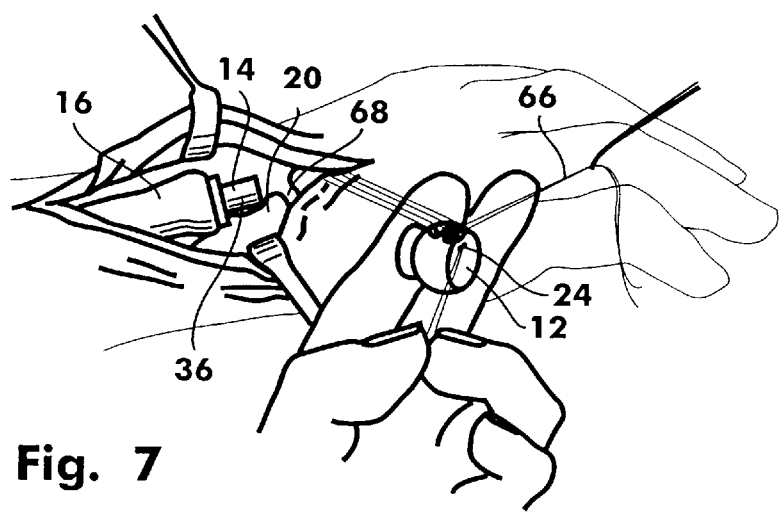
FIG. 7 is a perspective view of a forearm after insertion of the stem into the intramedullary canal and suturing of the head to the soft tissue that formerly surrounded the distal ulna.
Figure 8:
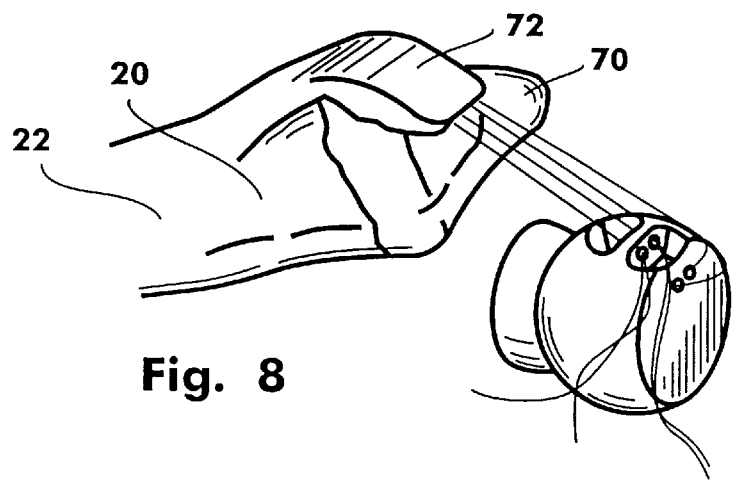
FIG. 8 is a perspective view of a radius and the soft tissue that formerly surrounded the distal ulna, showing the head after suturing to the soft tissue.
Figure 9:
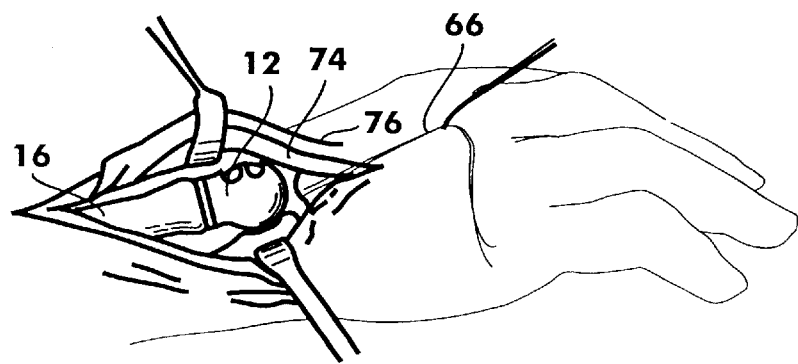
FIG. 9 is a perspective view of a forearm after attachment of the head to the stem.

Referring now to FIG. 7, the stem 14 is shown secured within the distal ulna 16. Once the stem 14 has been secured to the distal ulna 16, the head 12 can be sutured to the soft tissue formerly surrounding the distal ulna 16 using the suture holes 24 formed in the head 12. For this purpose, non-absorbable sutures 66 can be used. A minimum of five knotted suture passes with a 2.0 suture is preferred. As shown in FIGS. 7 and 8, the head 12 can be sutured to the soft tissues that formerly surrounded the distal ulna 16. Specifically, these soft tissues include the ulnar collateral capsule 68, the triangular fibrocartilage 70 and the extensor carpi ulnaris subsheath 72. Once the soft tissues are sutured to the head 12, the head 12 can be impacted onto the stem 14. Specifically, the distal end 36 of the stem 14 can be inserted into the bore 52 formed in the head 12. Next, the head 12 can be advanced onto the stem 14 with an impactor (not shown) until a secure fit is obtained between the head 12 and the stem 14. As shown in FIG. 9, after the head 12 is attached to the stem 14, the sutures 66 can be tied into the capsular sleeve surrounding the prosthesis 10 and the subcutaneous tissues 74 and skin 76 can be closed over the prosthesis 10.

While the particular Ulnar Implant System as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A prosthesis for implantation to replace the distal ulna in the forearm of a patient, after the resection of the distal ulna, wherein the resection exposes soft tissue that was formerly in contact with the distal ulna, said prosthesis comprising:

a head formed with a curved surface for articulation with the sigmoid notch of the distal radius, said head having at least one suture hole for anchoring said head to the soft tissue; and an elongated stem extending from said head, said stem having a proximal end and a distal end, said proximal end dimensioned for insertion into the intramedullary canal of the distal ulna to anchor said prosthesis to the ulna.

2. A device as recited in claim 1 wherein said stem is tapered toward said proximal end thereof with a proximally decreasing cross-section to facilitate the insertion of said stem into the intramedullary canal of the ulna and wherein said head is formed with a bore and said distal end of said stem is dimensioned for engagement with said bore of said head.

3. A device as recited in claim 1 wherein said stem is tapered toward said distal end thereof with a distally decreasing cross-section, and said bore of said head is tapered with a distally decreasing cross-section, said respective tapers being formed to secure said stem to said head when said distal end of said stem is engaged with said bore of said head.

4. A device as recited in claim 3 wherein said distal end taper and said bore taper are Morse tapers.

5. A device as recited in claim 1 wherein said proximal end is formed with at least one flute to prevent rotation of said stem in the intramedullary canal of the ulna.

6. A device as recited in claim 1 wherein said head is formed with four said suture holes.

7. A device as recited in claim 1 wherein said proximal end of said stem is formed with a surface for contact with the ulna, and said surface is textured to secure said stem to the ulna when said proximal end of said stem is inserted in the intramedullary canal of the ulna.

8. A device as recited in claim 1 wherein said stem is formed with a collar between said proximal end of said stem and said distal end of said stem, said collar formed with a proximal surface for buttressing said stem against said ulna.

9. A device as recited in claim 8 wherein said collar is approximately two millimeters (2 mm) between said distal surface and said proximal surface.

10. A device as recited in claim 8 wherein said collar is approximately twenty millimeters (20 mm) between said distal surface and said proximal surface for implantation of said prosthesis after a Darrach resection.

11. A prosthesis for implantation to replace the distal ulna in the forearm of a patient, after the resection of the distal ulna, wherein the resection exposes soft tissue that was formerly in contact with the distal ulna, said prosthesis comprising:

a head having a proximal end and formed with a surface, a portion of said surface being curved for articulation with the sigmoid notch of the distal radius, said surface of said head formed with a first indentation and a second indentation and having at least one suture hole extending from said first indentation to said second indentation for anchoring said head to the soft tissue; and an extension for projecting proximally from said proximal end of said head, said extension for anchoring said prosthesis in the intramedullary canal of the ulna.

12. A device as recited in claim 11 wherein said head is formed with an additional at least one suture hole extending from said first indentation to said surface of said head.

13. A device as recited in claim 11 wherein said head is formed with four suture holes, two said suture holes extending from said first indentation to said second indentation and two said suture holes extending from said first indentation to said surface of said head.

14. A method for establishing a distal ulnar prosthesis in a patient comprising the steps of:

exposing and resecting the distal ulna of the patient to expose the intramedullary canal of the ulna and the soft tissue that formerly surrounded the distal ulna;

providing a head formed with a curved surface for articulation with the sigmoid notch of the distal radius, said head formed with a bore and having at least one suture hole;

providing an elongated stem having a proximal end and a distal end;

inserting said stem into the intramedullary canal of the ulna to anchor said prosthesis to the ulna;

suturing said head to the soft tissue formerly surrounding the distal ulna; and inserting said distal end of said stem into said bore of said head.

15. A method as recited in claim 14 wherein nonabsorbable sutures are used to suture said head to the soft tissue formerly surrounding the distal ulna.

16. A method as recited in claim 14 wherein said head is sutured to the ulnar collateral capsule.

17. A method as recited in claim 14 wherein said head is sutured to the triangular fibrocartilage.

18. A method as recited in claim 14 wherein said head is sutured to the extensor carpi ulnaris subsheath.

19. A method as recited in claim 14 further comprising the step of using a template located distally over the articular surface of the distal ulna to mark the prescribed resection length.

20. A method as recited in claim 14 wherein said distal ulnar is exposed by making an incision along the medial shaft of the distal ulna in line with the ulnar styloid.

* * * * *